United States Patent [19]

Terrazas

[11] Patent Number: 5,411,471
[45] Date of Patent: May 2, 1995

[54] NECK RELAXER

[76] Inventor: Luis Terrazas, 157 Jeweled Mesa Rd., Santa Teresa, N. Mex. 88008

[21] Appl. No.: 141,395

[22] Filed: Oct. 22, 1993

[51] Int. Cl.⁶ .............................................. A61F 5/04
[52] U.S. Cl. ........................................ 602/18; 2/421
[58] Field of Search ................... 602/5, 15, 16, 17, 18, 602/19; 128/DIG. 23, 870; 2/2, 421, 422, 44, 45

[56] References Cited

U.S. PATENT DOCUMENTS

| | | | |
|---|---|---|---|
| 2,820,455 | 1/1958 | Hall | 602/18 |
| 3,873,996 | 4/1975 | Varteressian | 2/421 |
| 3,957,040 | 5/1976 | Calabrese | 128/75 |
| 4,194,501 | 3/1980 | Watt | 128/75 |
| 4,589,407 | 5/1986 | Koledin et al. | 128/87 |
| 4,593,788 | 6/1986 | Miller | 182/3 |
| 4,620,530 | 11/1986 | Lanier et al. | 128/75 |
| 4,628,913 | 12/1986 | Lerman | 128/78 |
| 4,913,135 | 4/1990 | Mattingly | 128/78 |
| 5,005,563 | 4/1991 | Veale | 128/75 |
| 5,027,833 | 7/1991 | Calkin | 128/870 |
| 5,046,490 | 9/1991 | Young et al. | 602/17 |
| 5,088,482 | 2/1992 | McGinness | 602/18 |
| 5,195,947 | 3/1993 | Bode | 602/18 |
| 5,201,702 | 4/1993 | Mars | 602/17 |

Primary Examiner—Richard J. Apley
Assistant Examiner—Beverly A. Meindl
Attorney, Agent, or Firm—R. Wayne Pritchard

[57] ABSTRACT

A portable brace for posterior support of the neck and upper back area consisting of back portion to which a movable neck portion is attached. The neck portion rotates in either the right or left direction and can be extended upwards to accommodate different neck dimensions. The back portion to which the neck portion is fastened fits over the shoulder area and extends downward to approximately the middle area of the back.

15 Claims, 5 Drawing Sheets

NECK RELAXER

FIELD OF INVENTION

The present invention relates to a portable neck brace designed to support but not immobilize the neck and head and also provide support to the upper back.

BACKGROUND OF THE INVENTION

The use of portable back and neck braces to immobilize the head and neck area subsequent to an injury has been widely used in the medical field for some time especially in the field of rehabilitation and physical therapy. Numerous United States Patents disclose neck and back braces—U.S. Pat. Nos. 3,957,040, 4,194,501, 4,589,407, 4,593,788, 4,620,530, 4,628,913, 4,913,135, 5,005,563, 5,027,833, 5,195,947, 5,201,702. The above patents disclose numerous designs for the immobilization of the neck and back area and, in general, fall into three (3) distinct catagories.

The first catagory can be referred to as the "halo traction" devices and include U.S. Pat. Nos. 5,195,947, 4,913,135, 4,628,913, 4,620,530, and 3,957,040. In such devices, a "halo" ring is positioned around the head of a patient and is attached to the skull by means of skull pins inserted through threaded holes in the "halo" ring. Contact with the patient's head is made by adjusting the skull pins inward. If the patient attempts to move his head, his skin will be pierced by the skull pins. The "halo traction" devices restrict head movement and place the head and neck area in traction.

The second catagory of devices can be referred to as the "ambulatory spine immobilizer" and include U.S. Pat. Nos. 5,027,833, 4,593,788, 4,589,407, and 4,194,501. The primary object of all such devices in this catagory is to provide a quick method for immobilizing the spine and cervical area in an emergency situation. Various methods of strapping the head and neck area to a rigid back supporting member are utilized in this catagory. The "ambulatory spine immobilizer" is not designed to be worn in other than an emergency, rescue situation.

The third catagory of devices involve inventions which like the previous two catagories immobilize the neck and cervical areas but unlike the previous two catagories are not utilized in emergency situations or through use of a "halo" mechanism. This catagory includes U.S. Pat. Nos. 5,201,702 and 5,005,563. The inventions disclosed in such patents involve a "U" shaped restraint which is designed to be placed around the patient's chin area fastened in some manner to a shoulder support mechanism.

The present invention is not designed for use in an emergency situation and does not utilize either the "halo" mechanism or the "U" shaped chin restraint. The present invention does not attempt to immobilize but instead provides support, only, to the neck, head and back area of a patient while at the same time maintains complete mobility as well as flexibility. While all of the three catagories of inventions disclosed above completely restrict a patient's movement of the neck in all directions, under the present invention, a patient's movement of the neck area would not be restricted in any direction other than towards the posterior and the neck and spinal regions of a patient would not be contacted by the brace components at all. Additionally, the upper support element can be removed from the lower support element allowing the user to utilize only the back support features of the brace. These aspects of the present invention, unlike any of the other catagories discussed above, allows use in normal daily activities.

SUMMARY OF INVENTION

According to the present invention, an apparatus for restricting the posterior movement of the neck and head area is provided. The apparatus includes a lower support element for supporting the back region of a human patient. The lower support element encompasses a substantial portion of the upper body. An upper support element is provided for supporting the neck and head area. Interconnecting means are employed to adjustably and detachably connect the lower support element to the upper support element. The upper support element can be removed from the lower support element, allowing the patient to utilize only the back support features of the brace.

In the preferred embodiment, the lower support element comprises a rear plate, a right front plate and a left front plate which conform to the upper back area. Padding is attached to the inside surfaces of the right and left front plates and to that portion of the rear plate outside the spinal area. Eliminating padding to that portion of the rear plate above the spinal area, reduces pressure to such area. The upper support element consists of a plate conforming to the back of the head area, proximate to the middle cerebellum area of the user.

Numerous advantages will be appreciated by those skilled in the art.

One advantage of the present invention is that it allows stability and support for the head and neck area without immobilizing such areas and without contacting or applying pressure to the neck or spinal regions of a patient. In particular, movement of the head and neck regions are restricted in the posterior direction while lateral/rotational movement of the head and neck area are permitted.

Another advantage of the present invention is that, in the preferred embodiment, the apparatus is of a lightweight construction insuring the user's ease of use and comfort during use and that it can be adjusted to fit any neck length, or shoulder width. Additionally, the upper support element can be removed, allowing the user to utilize only the back support features of the brace.

Yet another advantage of the present invention is that by not immobilizing the neck and head area of the user, the apparatus can be used throughout normal daily activities.

These and other features, advantages and objects of the present invention will be further understood and appreciated by those skilled in the art by reference to the following written specifications, claims and appended drawings.

DESCRIPTION OF THE PREFERRED EMBODIMENT

It is to be understood that the invention described below may assume various alternative orientations except where expressly specified to the contrary. It is also to be understood that the specific devices and processes illustrated in the attached drawings and described in the following specifications are simply exemplary embodiments of the inventive concepts defined in the appended claims. Hence, specific dimensions, and other physical characteristics related to the embodiments disclosed herein are not to be considered as limiting, unless the claims by their language expressly state otherwise.

Figure 1:
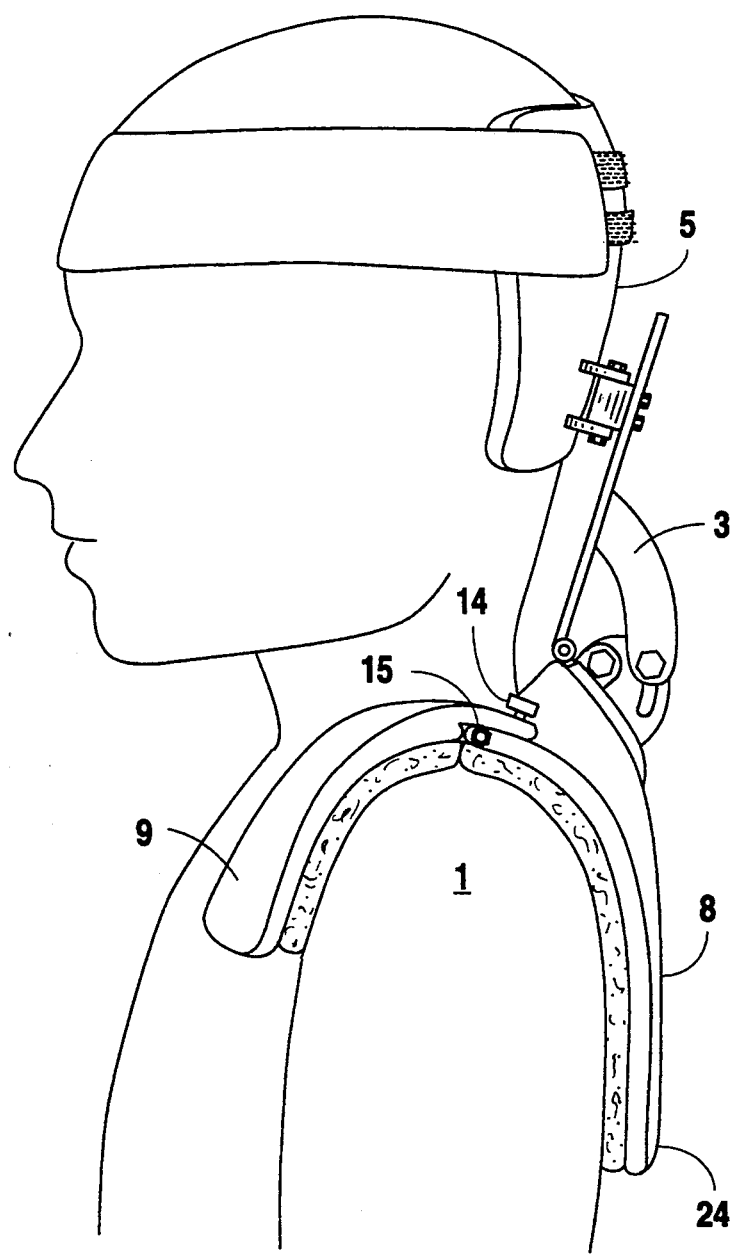
FIG. 1 is a side elevational view of the neck relaxer of the present invention as worn by a patient.

FIG. 1 depicts the orientation of the neck relaxer on a human patient. As can be seen from FIG. 1 and FIG. 2, said relaxer is positioned across the shoulders 1 and consists of an upper support element 5 for supporting the head region and a lower support element 24 for supporting the back area. In the preferred embodiement, the upper support element and lower support element are constructed of fiberglass. The lower support element 24 contains a rear plate 8, a right front plate 40, and a left front plate 9. The right front plate 40 and the left front plate 9 are secured to the rear plate by way of adjustable 14 hinged 15 mechanism. In the preferred embodiement, the right and left front plates are attached to the rear plate using bolts 41 which permit said plates to rotate in either the upward or downward directions. Once the right and left front plates are positioned for patient comfort, said plates are locked into position by adjusting the set screw 42 through the set screw hole 43.

The upper support element 5 and the lower support element 24 are adjustably and detachably connected together by way of a interconnecting device 3. In the preferred embodiement, the interconnecting device slides into a bracket 12 located on the rear plate and is tightened into place using a bolt 44.

Figure 4:
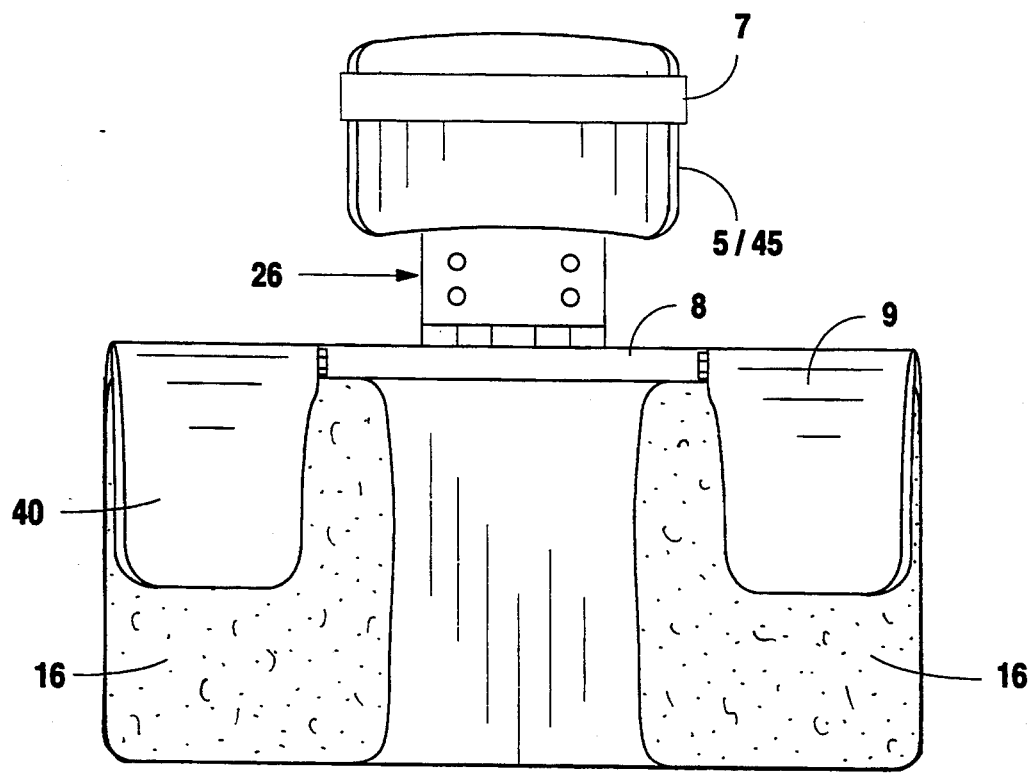
FIG. 4 is a frontal view of the present invention
Figure 5:
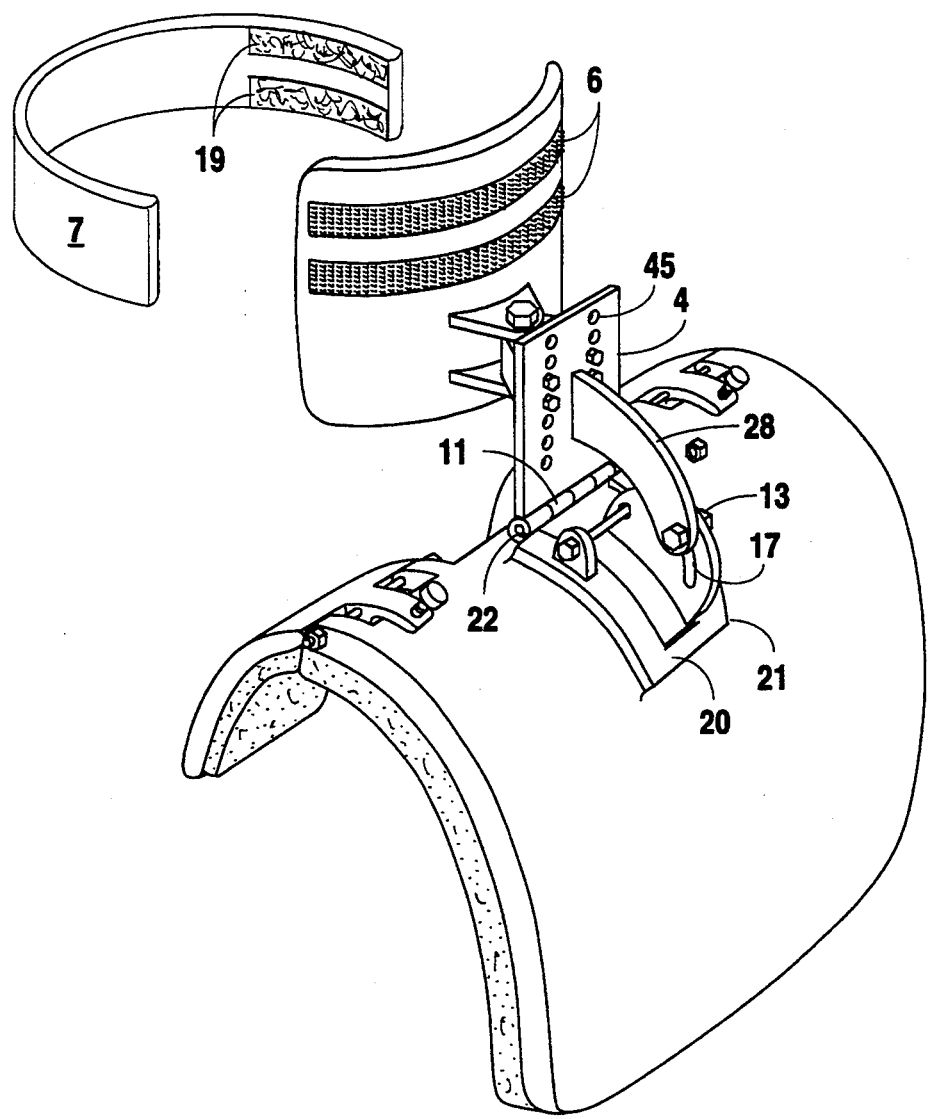
FIG. 5 is an isometric view of the present invention
Figure 6:
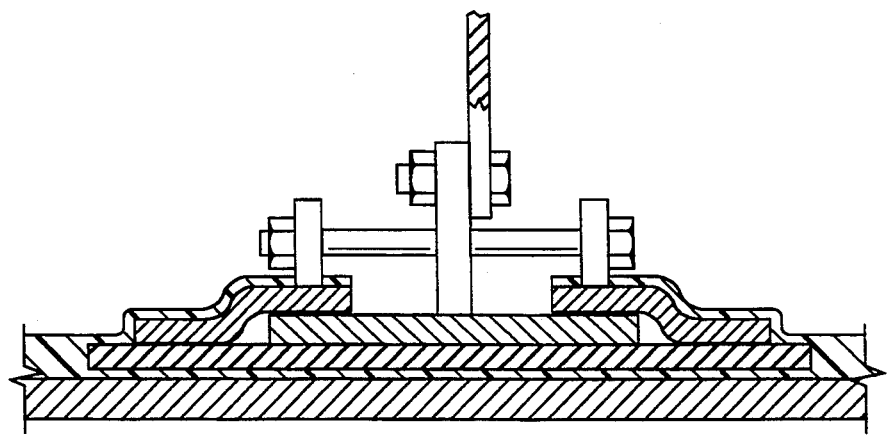
FIG. 6 is a detail of the attachment means between the back portion of the neck brace and the neck portion of said brace.

As shown in FIG. 4 and FIG. 5, a cushion material 16 is attached to inner surfaces of the rear plate 8 and the front plate 9 to reduce abrasion to the chest and back regions of a patient. In the preferred embodiement, the cushion material is sheepskin, although any padded material would function equally as well, and the sheepskin is attached to the front and rear plates using velcro-type hook and loop attachment strips 49.

The cushion material is attached to that portion of the inner surfaces of the rear plate outside the spinal area of a patient. This location of the cushion material on the rear plate keeps pressure from being exerted on the spinal area. The upper head of a patient is secured to the upper support element 5 through the use of a head strap 7 with attachment means 19 which connects to corresponding attachment means 6 on the upper support element 5. In the preferred embodiement, the head strap is attached to the upper support element using velcro-type hook and loop attachment strips 50.

Figure 7:
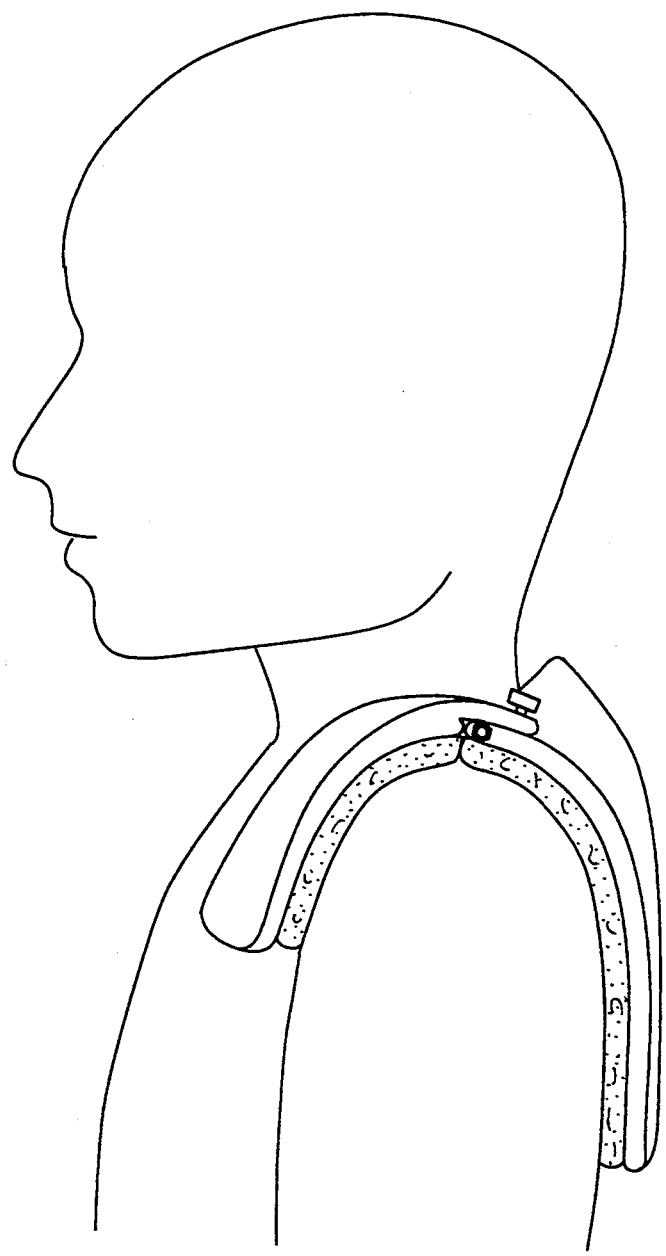
FIG. 7 is a side elevational view showing the neck relaxer with the upper support element removed.

FIG. 5 depicts the removeable interconnecting device 3 having a base plate 20 with a lower edge 21, an upper edge 22, and an eliptical opening 17; a neck plate 4 and an adjustable arm 28 secured to the eliptical opening 17 through use of a fastening means 13. The eliptical opening 17 allows the adjustable arm 28 to be moved in either the upward or downward directions. Once the adjustable arm is adjusted to fit the comfort needs of a patient, said arm is locked into place by tightening the fastening means. In the preferred embodiement, the fastening means is a bolt 47. FIG. 7 depicts the portable neck brace with the interconnecting device removed.

Figure 2:
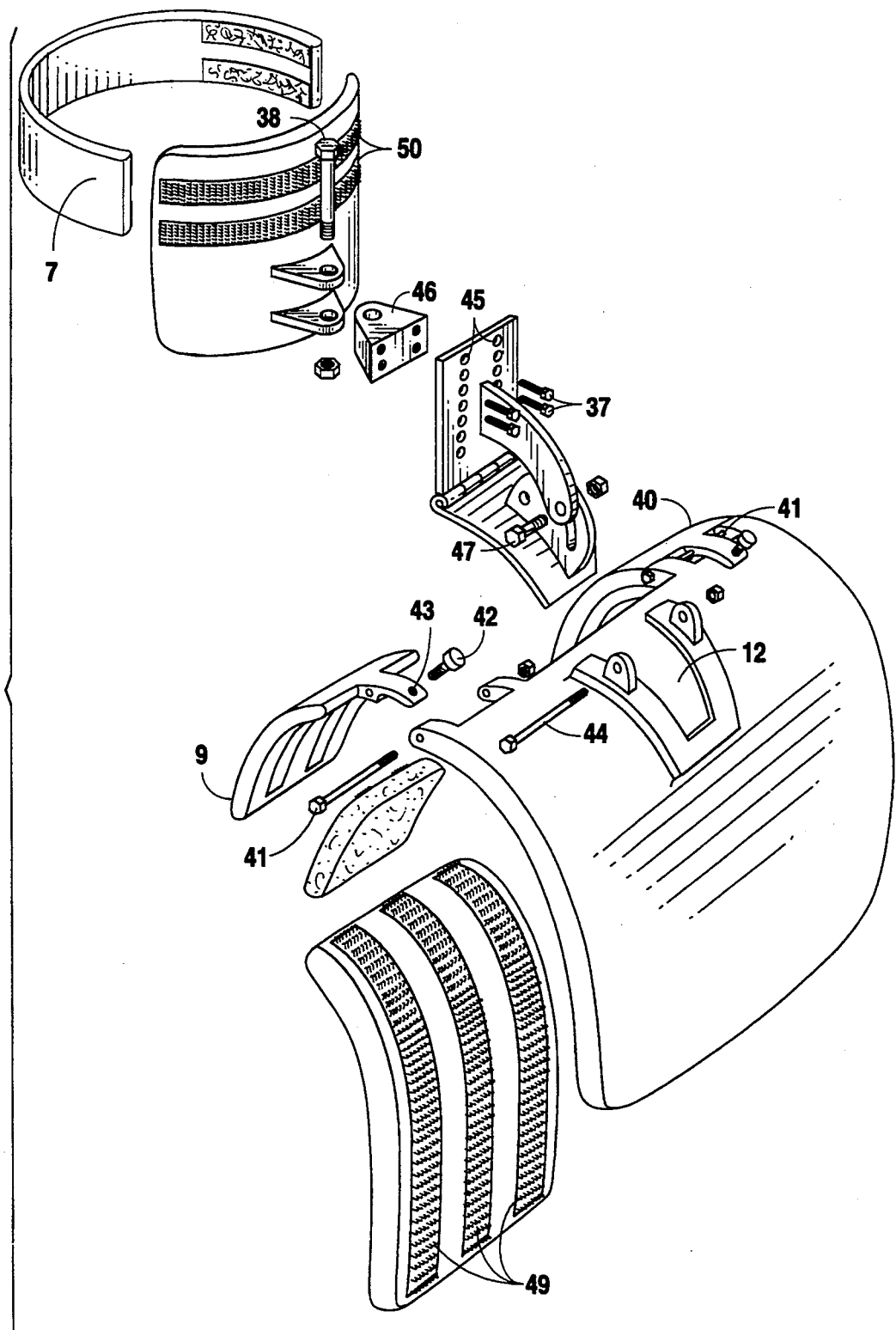
FIG. 2 is an exploded isometric view of the support means of the present invention.
Figure 3:
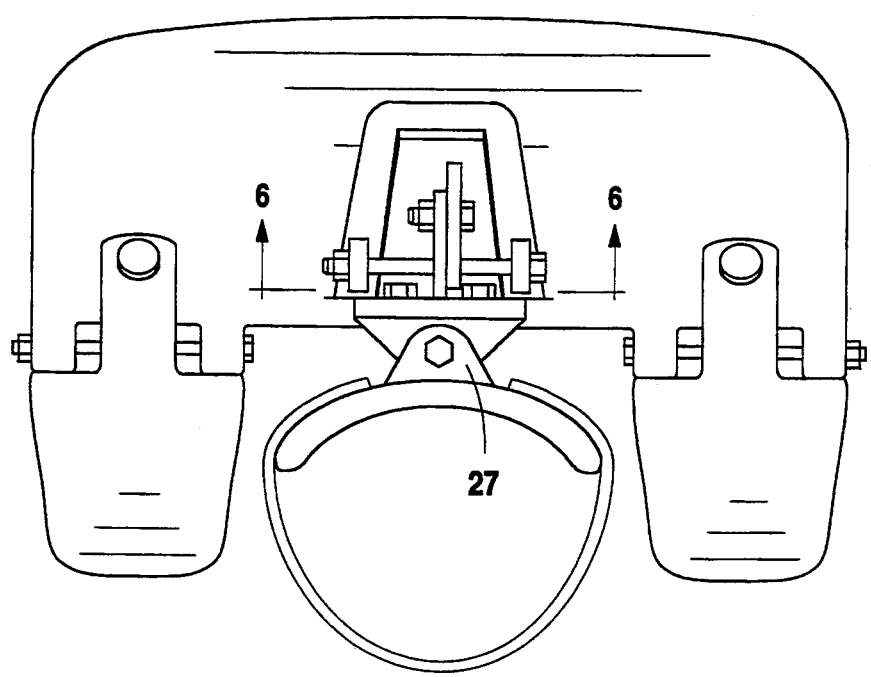
FIG. 3 is a top view of the present invention.

As can be seen from FIG. 2, FIG. 4 and FIG. 5, the upper edge 22 of the base plate 20 is attached to the neck plate 4 by way of a hinge 11 allowing the neck plate 4 to rotate in either the anterior or posterior direction. As can be seen from FIG. 2, the neck plate 4 is attached to the upper support element 5 through use of an intermediate connecting device 26 attached to the upper support element 5 by use of a pivot mechanism 27, allowing the upper support element to move in both lateral directions. In the preferred embodiement, the neck plate 4 contains numerous adjustment holes 45 for fastening the neck plate 4 to the swivel element 46. Once the patient's comfort needs are determined, the neck plate 4 and swivel element 46 are tightened together by placing bolts 37 through the adjustment holes 45. The swivel element 46 is attached to the pivot mechanism through use of a bolt 38 which is tightened into place once the comfort needs of a patient are determined.

In the foregoing description, it will be readily appreciated by those skilled in the art that modifications may be made to the invention without departing from the concepts disclosed herein. Such modifications are to be considered as included in the following claims unless those claims, by their language, expressly state otherwise.

I claim the following:

1. An apparatus for supporting the head, neck and back area of a human patient comprising:
   a. an upper support element for supporting the head, of the human patient;
   b. a lower support element for supporting the back of the human patient; and
   c. a means for attaching said upper support element to said lower support element which allows said upper support mechanism to rotate in both lateral directions relative to the head of said human patient about an axis of rotation which is situated in alignment and juxtaposed with the posterior region of the head of the human patient when said apparatus is worn by the human patient while restraining the upper support element in the posterior and anterior directions relative to the head of said human patient.

2. The apparatus as in claim 1 wherein said means for attaching said upper support element to said lower support element comprises a pivot mechanism whereby said upper support mechanism rotates around said pivot mechanism to allow said upper support mechanism to rotate in both lateral directions relative to the head of the human patient while restraining the upper support element in the posterior and anterior directions relative to the head of the human patient.

3. The apparatus as in claim 2 wherein said pivot mechanism has an axis of rotation which is substantially parallel to the spine of said human patient When said upper support element is worn by the human patient such that said head can rotate in both lateral directions about said axis of rotation while being restrained against motion in the anterior and posterior directions.

4. The apparatus as in claim 1 wherein said means for attaching said upper support element to said lower support element further comprises adjustment means so that the upper support element can be positioned to fit the head of the human patient correctly.

5. The apparatus as in claim 4 wherein said adjustment means allows the distance between the upper support element and the lower support element to be adjusted so that said upper support element can be positioned at the correct height to fit the head of the human patient.

6. The apparatus as in claim 4 wherein said adjustment means allows the angle of said upper support element to be adjusted relative to vertical so that said upper support element can be adjusted in the anterior and posterior directions relative to the head of the human patient.

7. The apparatus as in claim 1 further comprising a head strap connected to said upper support element which wraps around an upper portion of the head of the human patient to secure said head to said upper support element.

8. The apparatus as in claim 1 further comprising a cushion material attached to an inside surface of said lower support element at locations which are outside the spinal region of said patient, with no cushion material being attached to the inside surface of said lower support element at locations which are within the spinal region of said patient.

9. The apparatus as in claim 1 wherein said means for attaching said upper support element to said lower support element is detachable whereby said upper support element can be removed from said lower support element and said lower support element can be worn by itself to provide support to only the back area of the human patient.

10. The apparatus as in claim 9 wherein said means for attaching said upper support element to said lower support element comprises a slot means on said lower support element and a plate on said upper support element, wherein said plate slides into said slot means and is secured in place to detachable attach said upper support element to said lower support element.

11. The apparatus as in claim 1 wherein said lower support element comprises a rear plate, a right front plate and a left front plate.

12. The apparatus as in claim 11 wherein said right front plate and said left front plate are pivotally attached to said rear plate to allow adjustment thereof.

13. The apparatus as in claim 12 wherein said pivotal attachment between said left and right front plates and said rear plates further comprises a locking mechanism whereby said left front plate and said right front plate can be locked into a predetermined position.

14. The apparatus as in claim 13 wherein said rear plate, said right front plate and said left front plate comprise substantially rigid plates whereby, when said left front plate and said right front plate are locked into said predetermined position, said lower support element forms a substantially rigid unit and therefore provides support to the back area of the human patient.

15. The apparatus as in claim 13 wherein said upper support element is detachable from said lower support element whereby, when the upper support element is detached, the lower support element can be worn by itself to provide support to only the back area of the human patient.

* * * * *